(12) United States Patent
Bohme et al.

(10) Patent No.: US 6,350,768 B1
(45) Date of Patent: Feb. 26, 2002

(54) COMBINATION OF RILUZOLE AND OF GABAPENTIN AND ITS USE AS A MEDICAMENT

(75) Inventors: Andrees Bohme, Paris; Christopher Henderson, Cassis, both of (FR)

(73) Assignee: Aventis Pharma S.A., Antony Cedex (FR)

( * ) Notice: Subject to any disclaimer, the term of this patent is extended or adjusted under 35 U.S.C. 154(b) by 0 days.

(21) Appl. No.: 09/718,543

(22) Filed: Nov. 22, 2000

Related U.S. Application Data

(60) Provisional application No. 60/174,644, filed on Jan. 5, 2000.

(30) Foreign Application Priority Data

Nov. 24, 1999 (FR) ............................................. 99 14765

(51) Int. Cl.$^7$ ..................... A61K 31/425; A61K 31/195
(52) U.S. Cl. ........................................ 514/367; 514/561
(58) Field of Search ................................. 514/367, 561

(56) References Cited

FOREIGN PATENT DOCUMENTS

| EP | 0446570 | 9/1991 |
| EP | 0558861 | 9/1993 |

OTHER PUBLICATIONS

Louvel, E. et al: "Therapeutic Advances in Amyotrophic Lateral Sclerosis"; Trends in Pharmacological Sciences, GB, Elsevier Trends Journal, Cambridge, Jun. 1, 1997; vol. 18, No. 6; pp. 196–203.

Ross, M. A.: "Acquired Motor Neuron Disorders"; Neurologic Clinics, Aug., 1997; vol. 15, No. 3; pp. 481–500.

Mitsumoto, H. et al: "Druge Combination Treatment in Patients with ALS: Current Status and Future Directions"; Neurology, 1996; 47/4 Suppl. pp. S103–S107.

Lai, Eugene C.: "Therapeutic Developments in Amyotrophic Lateral Sclerosis"; Expert Opin. Invest. Drugs, 1999, pp. 347–361.

Lloyd–Williams, P. et al: "Convergent Solid–Phase Peptide Synthesis"; Tetrahedron, No. 347, 1993, p. 49.

Ciommer, M. et al: "Synthesis of Glyopeptides with Partial Structure of Human Glycophorin Using the Fluorenylmethoxycarbonyl Allyl Ester Protecting Group Combination"; SynLett, 1991, N8, pp. 593–595.

Lyttle, M. H. et al: "Peptides: Chemistry and Biology"; Proc. 12$^{th}$ American Peptide Symposium, 1992; p. 583.

Kates, S. A. et al: "Peptides: Chemistry, Structure and Biology" Proc. 13$^{th}$ American Peptide Symposium, 1994; p. 113.

*Primary Examiner*—William R. A. Jarvis
(74) *Attorney, Agent, or Firm*—Irving Newman

(57) ABSTRACT

The present invention relates to the combination of riluzole and of gabapentin or one of their pharmaceutically acceptable salts and its use as a medicament which is useful in particular for the prevention and/or treatment of motoneuron diseases.

10 Claims, No Drawings

COMBINATION OF RILUZOLE AND OF GABAPENTIN AND ITS USE AS A MEDICAMENT

CROSS REFERENCE TO RELATED APPLICATIONS

This application claims the benefit of U.S. Provisional Application No. 60/174,644, filed Jan. 5, 2000.

BACKGROUND OF THE INVENTION

The present invention relates to the combination of riluzole and of gabapentin or one of their pharmaceutically acceptable salts and its use as a medicament which is useful in particular for the prevention and/or treatment of motoneuron diseases.

Motoneuron diseases include in particular amyotrophic lateral sclerosis, progressive spinal amyotrophy, infantile spinal amyotrophy and primary lateral sclerosis. They are caused by a progressive loss of motoneurons in the spinal cord.

Amyotrophic lateral sclerosis (ALS), also known by the name of CHARCOT's disease and LOU GEHRIG's disease, was described for the first time by CHARCOT in 1865. It is the most important motoneuron disease. ALS is a fatal disease resulting from degeneration of the motoneurons. The disease is accompanied by progressive paralysis, leading to the loss of motor and respiratory functions and then to death within a period of two to eight years after the appearance of the first symptoms.

To date, only riluzole (2-amino-6-trifluoromethoxybenzothiazole) is marketed under the name RILUTEK® for the treatment of amyotrophic lateral sclerosis. Riluzole makes it possible mainly to slow down the progression of the disease.

Gabapentin has also been recommended for the treatment of neurodegenerative diseases and in particular of amyotrophic lateral sclerosis U.S. Pat. No. 5,084,479). Gabapentin is currently marketed under the name NEURONTIN® for the treatment of epilepsy.

DESCRIPTION OF THE INVENTION

It has now been found that the combination of riluzole and of gabapentin or one of their pharmaceutically acceptable salts makes it possible to increase the survival of the motoneurons more considerably than riluzole alone or gabapentin alone.

The effect of the combination has been studied on the cellular death of purified rat motoneurons which is induced by sera from patients suffering from amyotrophic lateral sclerosis.

Purified motoneurons prepared from the spinal cord of rat embryos at 14 days of gestation are cultured in the presence of optimum concentrations of recombinant "brain-derived neurotrophic factor" (BDNF), one of the principal neurotrophic factors for the survival of the motoneurons. 22 hours later, riluzole and gabapentin are added to the motoneurons either alone or in combination. After a further 2 hours, dilutions of dialyzed sera from patients suffering from ALS are added. On the next day, the number of surviving motoneurons is evaluated by direct counting under a phase contrast microscope.

Methods

Compounds

The stock solution of riluzole used in this test is prepared in the following manner: 5 mg of riluzole is added to 0.105 ml of a solution of hydrochloric acid (1M). The solution is stirred and then 2.1 ml of double distilled water is added.

The stock solution of gabapentin is prepared directly by dissolving 17.1 mg of gabapentin in 1 ml of double distilled water.

The solutions thus obtained can be stored at 4° C. for a maximum of 24 hours.

All the dilutions are freshly prepared in the complete culture medium, immediately before treating the cells.

Purification of the Motoneurons

Rat embryos at 14 days of gestation (Charles River, France) are recovered after sacrificing the mother, under $CO_2$ anesthesia, by pulling the neck. These embryos are placed in phosphate buffer ("phosphate-buffered saline", PBS) free of calcium and magnesium (Life Technologies).

A homogeneous population of purified motoneurons is obtained using the methods described by HENDERSON et al. [Henderson, C. E., Bloch-Gallego, E., and Camu, W. (1995). Purified embryonic motoneurons. In "Nerve cell culture: a practical approach" (J. Cohen and G. Wilkin, Eds.), pp. 69–81. Oxford University Press, London] and ARCE et al. [Arce, V., Garcès, A., de Bovis, B., Filippi, P., Henderson, C., Pettmann, B., and de Lapeyrière, O. (1999). Cardiotrophin-1requires LIFRbeta to promote survival of mouse motoneurons purified by a novel technique. *J. Neurosci. Res.* 55, 119–126]. Unless otherwise stated, the composition of the media used is identical to that indicated in these references. Spinal cords from rat embryos at 14 days of gestation are dissected in sterile PBS and the ventral halves of each cord containing the motoneurons are subdissected. They are then cut into small pieces with the aid of a scalpel and treated with trypsin (0.25%, weight/volume) in F10 medium free of calcium and of magnesium (Life Technologies). After 15 minutes, the trypsin is replaced with a complete culture medium L15 with no bicarbonate (marketed by Life Technologies, Inc.) and the spinal neurons are dissociated by a series of increasingly vigorous triturations. The trypsin and the cellular debris are separated by centrifugation through a layer of bovine serum albumin (BSA) at 4%. The first purification step is carried out on a gradient of 6.8% of metrizamide. The low-density fraction containing the motoneurons is centrifuged on a layer of BSA and then repurified by immuno-selection with the aid of a magnetic column (Miltenyi Biotech Inc.). For this purpose, the cells are resuspended in 50 μl of PBS +0.5% of BSA mixed with 50 μl of the antibody 192 which recognizes the low-affinity neurotrophin receptor $p75^{NTR}$ specifically expressed by the motoneurons at this stage of development. After incubating at 4° C. for 10 minutes, the motoneurons are centrifuged on BSA. The cells are again suspended in 80 μl of PBS +0.5% of BSA and 20 μl of magnetic beads grafted at the surface with anti-mouse rabbit antibodies, and then incubated at 4° C. for 15 minutes. The cells are then recentrifuged on BSA and transferred into a magnetic column. The eluted cells are large neurons; it being possible for 80 to 90% of them to be shown by immunolabeling to express the protein Islet-1, a marker specific for the motoneurons.

Culture of the Motoneurons

The purified motoneurons are inoculated at a density of 1000 motoneurons per well into 16-mm wells previously coated with polyornithine-laminin. The culture medium is the Neurobasal medium supplemented with complement B27 (Life Technologies) and 2% of horse serum but with no antibiotic, the total volume being 0.5 ml. The motoneurons are inoculated in the presence of neurotrophic factor BDNF (1 ng/ml; Sigma) and left in sedimentation for 22 hours during which they attach to the support and develop neurites. Riluzole ($3\times10^5$ M) and gabapentin ($3\times10^{-5}$ M) are added either separately or as a combination in a series of 4 wells. Two hours later, a dialyzed serum from patients suffering from ALS is added to the wells. The motoneurons are then cultured for 1 day at 37.2° C. before evaluating their survival.

Quantification of the Survival of the Motoneurons

The culture plates are removed from the incubator. The wells containing the motoneurons are completely filled with moderately warm L15 medium (Life Technologies). Their cover is then put back in place so as to form a horizontal meniscus allowing observation of the entire surface of the culture medium under phase contrast optical devices. For each well, the total number of motoneurons is counted along the two orthogonal diameters (x and y) of the field of the microscope. Given the fact that the presence of human serum changes the morphology of even the surviving motoneurons, all the cells carrying neurites and attached to the culture support are considered to be alive.

Analysis of the Data

The survival values (that is to say the number of motoneurons per well diameter) are calculated as the mean ±SEM of 8 measurements for 4 independent wells in each experiment.

The statistical analyses are carried out using a Student test (t-test).

The results obtained are mentioned in the following table:

| ALS serum | 0% | 0.1% | 0.1% | 0.1% | 0.1% |
|---|---|---|---|---|---|
| Riluzole (M) | 0 | 0 | $3 \times 15^{-5}$ | 0 | $3 \times 15^{-5}$ |
| Gabapentin (M) | 0 | 0 | 0 | $10^{-5}$ | $10^{-5}$ |
| Number of | 13 | 3 | 7 | 6 | 12 |
| motoneurons (per | 26 | 4 | 9 | 5 | 19 |
| experiment and | 19 | 0 | 4 | 5 | 18 |
| per well | 36 | 4 | 9 | 9 | 17 |
| diameter) | 33 | 2 | 11 | 2 | 18 |
|  | 33 | 4 | 7 | 9 | 14 |
|  | 25 | 5 | 6 | 1 | 23 |
|  | 32 | 2 | 7 | 3 | 21 |
| Mean | 27.1 | 3.0 | 7.5 | 5.0 | 17.8 |
| (± SEM) | ±2.8 | ±0.6 | ±0.8* | ±1.1* | ±1.3** |

*$p = 0.0003$
**$p < 00001$

BDNF (1 ng/ml) is added to all the experiments as mentioned in the general technique. These results demonstrate that:

a—the serum from a patient suffering from ALS induces the death of 89% of the motoneurons even in the presence of neurotrophic support, therefore leaving 11% of surviving neurons.

b—when the medium is treated with riluzole alone, the survival of the motoneurons is 19% c—when the medium is treated with gabapentin alone, the survival of the motoneurons is 8% d—when the medium is treated with the combination of riluzole and of gabapentin, the survival of the motoneurons is 61%, thus demonstrating a synergy between the two molecules.

Riluzole may be prepared according to the method described in U.S. Pat. No. 4,370,338.

Gabapentin may be prepared according to the method described in Patents FR 2,294,697 and U.S. Pat. No. 4,024,175.

As pharmaceutically acceptable salts of riluzole and of gabapentin, there may be mentioned in particular the addition salts with inorganic acids such as hydrochloride, sulfate, nitrate, phosphate or organic acids such as acetate, propionate, succinate, oxalate, benzoate, fumarate, maleate, methanesulfonate, isethionate, theophilline acetate, salicylate, phenolphthalinate, methylene-bis-β-oxynaphthoate or substitution derivatives of these derivatives.

The combination may be used by the oral, parenteral or rectal route, either simultaneously or separately or spaced out over time.

The present invention also relates to the pharmaceutical compositions comprising the combination of riluzole and of gabapentin or one of their pharmaceutically acceptable salts, in the pure state or in the form of a combination with one or more compatible and pharmaceutically acceptable diluents and/or adjuvants and/or optionally in combination with another pharmaceutically compatible and physiologically active product.

As solid compositions for oral administration, use may be made of tablets, pills, powders (gelatin capsules, cachets) or of granules. In these compositions, the active ingredients are mixed with one or more inert diluents, such as starch, cellulose, sucrose, lactose or silica, under an argon stream. These compositions may also comprise substances other than the diluents, for example one or more lubricants such as magnesium stearate or talc, a coloring, a coating (sugar-coated tablets) or a glaze.

As liquid compositions for oral administration, use may be made of pharmaceutically acceptable solutions, suspensions, emulsions, syrups and elixirs containing inert diluents such as water, ethanol, glycerol, vegetable oils or paraffin oil. These compositions may comprise substances other than the diluents, for example wetting products, sweeteners, thickeners, flavorings or stabilizers.

The sterile compositions for parenteral administration may be preferably solutions which are aqueous or nonaqueous, suspensions or emulsions. As solvent or vehicle, use may be made of water, propylene glycol, polyethylene glycol, vegetable oils, in particular olive oil, injectable organic esters, for example ethyl oleate or other suitable organic solvents. These compositions may also contain adjuvants, in particular wetting, isotonizing, emulsifying, dispersing and stabilizing agents. The sterilization may be performed in several ways, for example by asepticizing filtration, by incorporating into the composition sterilizing agents, by irradiation or by heating. They may also be prepared in the form of sterile solid compositions which may be dissolved at the time of use in sterile water or any other injectable sterile medium.

The compositions for rectal administration are suppositories or rectal capsules which contain, in addition to the active ingredient, excipients such as cocoa butter, semisynthetic glycerides or polyethylene glycols.

The present invention also relates to the use of the combination of riluzole and of gabapentin or one of their pharmaceutically acceptable salts for the preparation of a medicament useful for the prevention and/or treatment of motoneuron diseases and, in particular, amyotrophic lateral sclerosis, progressive spinal amyotrophy, infantile spinal amyotrophy or primary lateral sclerosis.

The present invention also relates to the method of preventing and/or of treating patients suffering from motoneuron diseases and, in particular, from amyotrophic lateral sclerosis, progressive spinal amyotrophy, infantile spinal amyotrophy or primary lateral sclerosis which consists in administering to the patient a combination of riluzole and of gabapentin or one of their pharmaceutically acceptable salts either simultaneously or separately or spaced out over time.

The doses depend on the desired effect, the duration of the treatment and the route of administration used; they are generally from 10 to 400 mg per day by the oral route for an adult with unit doses ranging from 10 to 200 mg of riluzole and from 100 to 2400 mg per day by the oral route for an adult with unit doses of 100 to 400 mg of gabapentin.

In general, the doctor will determine the appropriate dosage according to the age, weight and all the other factors specific to the subject to be treated.

What is claimed is:

1. A pharmaceutical composition or kit, comprising, in combination, riluzole and gabapentin or a pharmaceutically acceptable salt thereof, in synergistically effective amounts to promote motoneuron survival.

2. The combination according to claim 1, in which said riluzole or salt thereof is present in an amount of 10 to 400 parts by weight per 300 to 2400 parts by weight of said gabapentin or salt thereof.

3. The pharmaceutical composition of claim 1, which further comprises at least one compatible and pharmaceutically acceptable diluent or adjuvant.

4. A method for the prevention or treatment of a motoneuron disease in a patient in need thereof comprising administering to said patient a combination according to claim 1.

5. A method for the prevention or treatment of amyotrophic lateral sclerosis in a patient in need thereof comprising administering to said patient a combination according to claim 1.

6. A method for the prevention or treatment of a disease selected from the group consisting of progressive spinal amyotrophy, infantile spinal amyotrophy and primary lateral sclerosis in a patient in need thereof comprising administering to said patient a combination according to claim 1.

7. The combination of claim 1 in the form of a kit in which said riluzole or salt thereof is packaged separately from said gabapentin or salt thereof.

8. The combination of claim 1 in which said riluzole or salt thereof and said gabapentin or salt thereof are combined in a single pharmaceutically acceptable composition.

9. The method according to claim 4, in which said combination is administered simultaneously.

10. The method according to claim 4, in which the times of administration of the riluzole drug and of the gabapentin drug of said combination are spaced out over time.

* * * * *